US007884049B2

(12) United States Patent
Dutzmann et al.

(10) Patent No.: US 7,884,049 B2
(45) Date of Patent: Feb. 8, 2011

(54) COMPOSITIONS FOR THE CONTROL OF PLANT PESTS

(75) Inventors: Stefan Dutzmann, Langenfeld (DE); Christopher Erdelen, Leichlingen (DE); Angelika Lubos-Erdelen, legal representative, Leichlingen (DE); Wolfram Andersch, Bergisch Gladbach (DE); Heinz-Wilhelm Dehne, Bonn (DE); Jürgen Hartwig, Leichlingen (DE); Klaus Stenzel, Düsseldorf (DE); Wolfgang Krämer, Burscheid (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 12/776,345

(22) Filed: May 7, 2010

(65) Prior Publication Data

US 2010/0210691 A1 Aug. 19, 2010

Related U.S. Application Data

(62) Division of application No. 12/515,339, filed on May 18, 2009, which is a division of application No. 11/284,246, filed on Nov. 21, 2005, which is a division of application No. 10/160,887, filed on Jun. 3, 2002, now Pat. No. 7,008,903, which is a division of application No. 09/911,263, filed on Jul. 23, 2001, now Pat. No. 6,423,726, which is a division of application No. 09/585,227, filed on Jun. 1, 2000, now Pat. No. 6,297,263, which is a division of application No. 08/765,819, filed as application No. PCT/EP95/02799 on Jul. 17, 1995, now Pat. No. 6,114,362.

(30) Foreign Application Priority Data

Jul. 28, 1994 (DE) ................................. 44 26 753

(51) Int. Cl.
*A01N 43/40* (2006.01)
*A01N 37/20* (2006.01)
*A01N 37/22* (2006.01)
*A01N 37/46* (2006.01)

(52) U.S. Cl. .................. 504/100; 514/341; 514/538
(58) Field of Classification Search .................. 514/341, 514/538; 504/100
See application file for complete search history.

(56) References Cited

U.S. PATENT DOCUMENTS

| 3,341,403 A | 9/1967 | Klauke et al. |
| 3,912,752 A | 10/1975 | Meiser et al. |
| 3,952,002 A | 4/1976 | Kramer et al. |
| 4,048,318 A | 9/1977 | Meiser et al. |
| 4,147,791 A | 4/1979 | Meiser et al. |
| 4,532,341 A | 7/1985 | Holmwood et al. |
| 4,590,272 A | 5/1986 | Shiokawa et al. |
| 4,647,570 A | 3/1987 | Shiokawa et al. |
| 4,678,795 A | 7/1987 | Shiokawa et al. |
| 4,680,294 A | 7/1987 | Shiokawa et al. |
| 4,731,385 A | 3/1988 | Tsuboi et al. |
| 4,742,060 A | 5/1988 | Shiokawa et al. |
| 4,742,079 A | 5/1988 | Devoise-Lambert et al. |
| 4,772,620 A | 9/1988 | Shiokawa et al. |
| 4,806,553 A | 2/1989 | Shiokawa et al. |
| 4,845,106 A | 7/1989 | Shiokawa et al. |
| 4,849,432 A | 7/1989 | Shiokawa et al. |
| 4,882,344 A | 11/1989 | Shiokawa et al. |
| 4,897,107 A | 1/1990 | Holmwood et al. |
| 4,914,113 A | 4/1990 | Shiokawa et al. |
| 4,918,086 A | 4/1990 | Gsell |
| 4,945,111 A | 7/1990 | Lunkenheimer et al. |
| 4,948,798 A | 8/1990 | Gsell |
| 4,963,572 A | 10/1990 | Gsell |
| 5,034,404 A | 7/1991 | Uneme et al. |
| 5,034,524 A | 7/1991 | Shiokawa et al. |
| 5,039,686 A | 8/1991 | Davies et al. |
| 5,077,306 A | 12/1991 | Lunkenheimer et al. |
| 5,302,605 A | 4/1994 | Kristiansen et al. |
| 5,601,847 A | 2/1997 | Bassi |
| 5,648,383 A | 7/1997 | Nuninger et al. |
| 5,723,491 A | 3/1998 | Nuninger et al. |
| 5,750,130 A | 5/1998 | Ferrell et al. |
| 5,883,045 A | 3/1999 | Wada et al. |
| 5,972,971 A | 10/1999 | Heuer et al. |
| 5,990,043 A | 11/1999 | Kugler et al. |
| 6,114,362 A | 9/2000 | Dutzmann et al. |
| 6,297,263 B1 | 10/2001 | Dutzmann et al. |
| 6,306,414 B1 | 10/2001 | Koike |

(Continued)

FOREIGN PATENT DOCUMENTS

AU 2139083 5/1984

(Continued)

OTHER PUBLICATIONS

Abstract of German Publication No. DD 140 412, Lehmann, H., et al., published Mar. 5, 1980.
Abstract of Japanese Publication No. JP 58124703, Sumitomo Chemical Co., published Jul. 25, 1983.
Abstract of Japanese Publication No. JP 61267575, Nihon Tokushu Noyaku Seizo K.K., published Nov. 27, 1986.
Abstract of Japanese Publication No. JP 62099311, Nihon Tokushu Noyaku Seizo K.K., published May 8, 1987.

(Continued)

*Primary Examiner*—John Pak
(74) *Attorney, Agent, or Firm*—Sterne, Kessler, Goldstein & Fox P.L.L.C.

(57) ABSTRACT

The present invention provides a composition comprising imidacloprid and metalaxyl. The compositions of the present invention find use as pesticides.

12 Claims, No Drawings

U.S. PATENT DOCUMENTS

| | | | |
|---|---|---|---|
| 6,423,726 B2 | 7/2002 | Dutzmann et al. | |
| 6,875,727 B2 * | 4/2005 | Hofer | 504/100 |
| 7,008,903 B2 | 3/2006 | Dutzmann et al. | |
| 7,071,188 B2 * | 7/2006 | Watrin | 514/229.2 |
| 7,307,070 B2 | 12/2007 | Heuer et al. | |
| 7,807,714 B2 * | 10/2010 | Brandl et al. | 514/533 |
| 2002/0173529 A1 | 11/2002 | Dutzmann et al. | |
| 2005/0009703 A1 | 1/2005 | Wachendorff-Neumann et al. | |
| 2005/0009883 A1 | 1/2005 | Uhr et al. | |
| 2006/0004070 A1 | 1/2006 | Wachendorff-Neumann et al. | |
| 2006/0014738 A1 | 1/2006 | Wachendorff-Neumann et al. | |
| 2006/0035942 A1 | 2/2006 | Wachendorff-Neumann et al. | |
| 2006/0079401 A1 | 4/2006 | Dutzmann et al. | |
| 2006/0276342 A1 | 12/2006 | Krahmer et al. | |
| 2007/0010399 A1 | 1/2007 | Rosinger et al. | |
| 2007/0037799 A1 | 2/2007 | Dahmen et al. | |
| 2007/0054804 A1 | 3/2007 | Suty-Heinze | |
| 2007/0078171 A1 | 4/2007 | Andersch et al. | |
| 2007/0142327 A1 | 6/2007 | Funke et al. | |
| 2007/0155797 A1 | 7/2007 | Andersch et al. | |
| 2007/0203025 A1 | 8/2007 | Bickers et al. | |
| 2007/0213396 A1 | 9/2007 | Thielert et al. | |
| 2007/0232598 A1 | 10/2007 | Funke et al. | |
| 2007/0270416 A1 | 11/2007 | Funke et al. | |
| 2008/0027114 A1 | 1/2008 | Funke et al. | |
| 2008/0070863 A1 | 3/2008 | Funke et al. | |
| 2008/0261811 A1 | 10/2008 | Krohn et al. | |
| 2008/0269051 A1 | 10/2008 | Suty-Heinze et al. | |
| 2008/0269263 A1 | 10/2008 | Dahmen et al. | |
| 2008/0274882 A1 | 11/2008 | Krohn et al. | |
| 2009/0156399 A1 | 6/2009 | Hungenberg et al. | |
| 2009/0215760 A1 | 8/2009 | Hungenberg et al. | |
| 2009/0247511 A1 | 10/2009 | Suty-Heinze et al. | |
| 2009/0281151 A1 | 11/2009 | Hungenberg et al. | |
| 2009/0286681 A1 | 11/2009 | Dahmen et al. | |

FOREIGN PATENT DOCUMENTS

| | | |
|---|---|---|
| AU | 2978992 | 6/1993 |
| DE | 140 412 | 3/1980 |
| DE | 37 12 307 A1 | 10/1988 |
| EP | 0 040 345 A1 | 11/1981 |
| EP | 0 112 284 A2 | 6/1984 |
| EP | 0 135 956 A2 | 4/1985 |
| EP | 0 136 636 A2 | 4/1985 |
| EP | 0 154 178 A1 | 9/1985 |
| EP | 0 163 855 A1 | 12/1985 |
| EP | 0 189 972 A1 | 8/1986 |
| EP | 0 192 060 A2 | 8/1986 |
| EP | 0 212 600 A2 | 3/1987 |
| EP | 0 235 725 A2 | 9/1987 |
| EP | 0 254 859 A2 | 2/1988 |
| EP | 0 259 738 A2 | 3/1988 |
| EP | 0 302 389 A2 | 2/1989 |
| EP | 0 302 833 A2 | 2/1989 |
| EP | 0 303 570 A2 | 2/1989 |
| EP | 0 304 758 A1 | 3/1989 |
| EP | 0 306 696 A1 | 3/1989 |
| EP | 0 315 826 A1 | 5/1989 |
| EP | 0 364 844 A1 | 4/1990 |
| EP | 0 375 907 A1 | 7/1990 |
| EP | 0 382 375 A2 | 8/1990 |
| EP | 0 383 091 A1 | 8/1990 |
| EP | 0 425 978 A2 | 5/1991 |
| EP | 0 428 941 A1 | 5/1991 |
| EP | 0 455 000 A1 | 11/1991 |
| EP | 0 464 830 A1 | 1/1992 |
| EP | 0 471 372 A1 | 2/1992 |
| EP | 0 511 541 A1 | 11/1992 |
| EP | 0 545 834 A1 | 6/1993 |
| EP | 0 565 354 A1 | 10/1993 |
| EP | 0 591 764 A1 | 4/1994 |
| EP | 0 705 160 | 1/1995 |
| JP | 48080738 | 10/1973 |
| JP | 50013534 | 2/1975 |
| JP | 58124703 | 7/1983 |
| JP | 61267575 | 11/1986 |
| WO | WO 91/04965 A1 | 4/1991 |
| WO | WO 91/17659 A1 | 11/1991 |
| WO | WO 92/21241 A1 | 12/1992 |
| WO | WO 94/00013 | 1/1994 |

OTHER PUBLICATIONS

Abstract of Japanese Publication No. JP 63068505, Nihon Tokushu Noyaku Seizo K.K., published Mar. 28, 1988.
Abstract of Japanese Publication No. JP 63068507, Nihon Tokushu Noyaku Seizo K.K., published Mar. 28, 1988.
Abstract of Japanese Publication No. JP 63072608, Nihon Tokushu Noyaku Seizo K.K., published Apr. 2, 1988.
Abstract of Japanese Publication No. JP 63072609, Nihon Tokushu Noyaku Seizo K.K., published Apr. 2, 1988.
Abstract of Japanese Publication No. JP 63072610, Nihon Tokushu Noyaku Seizo K.K., published Apr. 2, 1988.
Abstract of Japanese Publication No. JP 63150204, Nihon Tokushu Noyaku Seizo K.K., published Jun. 22, 1988.
Abstract of Japanese Publication No. JP 63150205, Nihon Tokushu Noyaku Seizo K.K., published Jun. 22, 1988.
Abstract of Japanese Publication No. JP 63154602, Nihon Tokushu Noyaku Seizo K.K., published Jun. 27, 1988.
Abstract of Japanese Publication No. JP 63156705, Nihon Tokushu Noyaku Seizo K.K., published Jun. 29, 1988.
Abstract of German Publication No. DE 37 12 307, Bayer AG, published Oct. 20, 1988.
Abstract of Japanese Publication No. JP 63287764, Nihon Tokushu Noyaku Seizo K.K., published Nov. 24, 1988.
Abstract of Japanese Publication No. JP 63307857, Nihon Tokushu Noyaku Seizo K.K., published Dec. 15, 1988.
Abstract of Japanese Publication No. JP 1006203, Nihon Tokushu Noyaku Seizo K.K., published Jan. 10, 1989.
Abstract of Japanese Publication No. JP 2207083, Nihon Tokushu Noyaku Seizo K.K., published Aug. 16, 1990.
Abstract of Japanese Publication No. JP 3044304, Takeda Chemical Industries Ltd., published Feb. 26, 1991.
Abstract of Japanese Publication No. JP 3047106, Nihon Tokushu Noyaku Seizo K.K., published Feb. 28, 1991.
Abstract of Japanese Publication No. JP 3220176, Nihon Tokushu Noyaku Seizo K.K., published Sep. 27, 1991.
Abstract of Japanese Publication No. JP 3255072, Nippon Soda Co., published Nov. 13, 1991.
Abstract of Japanese Publication No. JP 3271207, Bayer Agrochem K.K., published Dec. 3, 1991.
Abstract of Japanese Publication No. JP 4108704, Takeda Chemical Industries Ltd., published Apr. 9, 1992.
Abstract of Japanese Publication No. JP 4360804, Nippon Soda Co., published Dec. 14, 1992.
Abstract of Japanese Publication No. JP 4368303, Nippon Soda Co., published Dec. 21, 1992.
Abstract of Japanese Publication No. JP 4368304, Nippon Soda Co., published Dec. 21, 1992.
Abstract of Japanese Publication No. JP 3279359, Nihon Tokushu Noyaku Seizo K.K., published Dec. 10, 1991.
Abstract of Japanese Publication No. JP 5017311, Nippon Soda Co., published Jan. 26, 1993.
Abstract of Japanese Publication No. JP 5032505, Bayer Agrochem K.K., published Feb. 9, 1993.
Abstract of European Publication No. EP 0 545 834, Rhone-Poulenc Agrochimie, published Jun. 9, 1993.
Bartlett, D.H., "Review of Current and Future Seed Treatment Usage in Oilseed Rape," *BCPC Monograph* 57:159-168 (1994).
Blackshaw, R.E., "HOE-39866 Use in Chemical Fallow Systems," *Weed Tech*. 3:420-428, The Weed Science Society of America (1989).

Blackshaw, R.E., "Synergistic Mixes of DPX-A7881 and Clopyralid in Canola (*Brassica napus*)," *Weed Tech.* 3:690-695, The Weed Science Society of America (1989).

Blackshaw, R.E., et al., "Herbicide Combinations for Postemergent Weed Control in Safflower (*Carthamus tinctorius*)," *Weed Tech.* 4:97-104, The Weed Science Society of America (1990).

Büchel, K.H., Pflanzenschutz and Schädlingbekämpfung, pp. 121-153 (George Thieme Verlag Stuttgart 1977).

Abstract of Cabello, T., et al., "Mixture of pesticidal products used in horticultural crops in greenhouses of SE Spain. Analysis of costs.," *Bol. Sanid. Veg. Plagas* 20:429-436 (1994).

Flint, J.L., et al., "Analyzing Herbicide Interactions, A Statistical Treatment of Colby's Method," *Weed Tech.* 2:304-309, The Weed Science Society of America (1988).

Gillespie, G.R. and Nalewaja, J.D., "Wheat (Triticum aestivum) Response to Triallate Plus Chlorsulfuron," *Weed Tech.* 3:20-23, The Weed Science Society of America (1989).

Green, J.M., et al., "Metribuzin and Chlorimuron Mixtures for Preemergence Broadleaf Wheat Control in Soybeans, Glycine max," *Weed Tech.* 2:355-363, The Weed Science Society of America (1988).

Handbook of Agricultural Chemicals, pp. 534-543, 560, and 563 (Japan Plant Protection Association 1992).

Harker, N.K., and O'Sullivan, P.A., "Synergistic Mixtures of Sethoxydim and Fluazifop on Annual Grass Weeds," *Weed Tech.* 5:310-316, The Weed Science Society of America (1991).

Harveson, R.M., et al., "Seed Treatment with Tachigaren for Controlling Blac Root of Sugar Beet, 1993," *Fungic. Nematic. Tests* 49:277, The American Phytopathological Society (1994).

Jardine, D.J., et al., "Effect of seed treatment fungicides on stand and yield of soybeans," *Fungic. Nematic. Tests* 49:289, The American Phytopathological Society (1994).

Kent, L.M., et al., "Effect of Ammonium Sulfate, Imazapyr, and Environment on the Phytotoxicity of Imazethapyr," *Weed Tech.* 5:202-205, The Weed Science Society of America (1991).

CABA Abstract 74:28293 for Kolbe, W., "Studies to evaluate Euparen M as a fungicidal treatment of pome fruit, with special consideration to its acaricidal action and varietal tolerance," *Pflanzenschutz-Nachrichten Bayer* 25:123-162 (1972).

Pike, K.S., "Compatibility of Imidacloprid with Fungicides as a Treatment Control of Russian Wheat Aphid (Homo Aphididae) and Effect on Germination, Growth, Yield of Wheat and Barley," *J. Econ. Entomol.* 86:586-593, Entomological Society of America (1993).

Salzmann, F.P. and Renner, K.A., "Response of Soybean to Combinations of Clomazone, Metribuzin, Linuron, Alachlor, and Atrazine," *Weed Tech.* 6:922-929, The Weed Science Society of America (1992).

Sloderbeck, P.E., et al., "Seed Treatment Evaluated for Greenbug Control in Sorghum, 1993," *Arthropod Management Tests* 19:265, Entomological Society of America, Lanham, MD (1994).

Sloderbeck, P.E., et al., "Seed Treatment Evaluated for Greenbug Control in Sorghum, 1994," *Arthropod Management Tests* 20:233-234, Entomological Society of America, Lanham, MD (1995).

Stansly, P.A., "Protection of the Young Citrus Trees from Damage by Subterranean Termites," *Proc. Fla. State Hortic. Soc.* 105:7-10 (1992).

Abstract of Taborsky, V., et al., "The toxic effect of different pesticides on the predatory bug, Orius majusculus (Heteroptera: Anthocoridae)," *Ochrana Rostlin* 31:257-263 (1995).

Unverified English language translation of Notice of Reasons for Rejection issued by the Japanese Patent Office for Japanese Patent Application No. 37607505 (mailed Feb. 6, 2007).

Unverified English language translation of WO 92/21241, Nippon Soda Co., Ltd., published Dec. 10, 1992 (cited herein as document FP 38).

Co-pending U.S. Appl. No. 10/581,348 inventors Funke, C., et al., filed Nov. 20, 2004 (Not Yet Published).

Co-pending U.S. Appl. No. 11/910,659 inventors Wachendorff-Neumann, U., et al., filed Mar. 27, 2007 (Not Yet Published).

Co-pending U.S. Appl. No. 12/515,339 inventors Dutzmann, S., et al., filed May 18, 2009 (Not Yet Published).

Co-pending U.S. Appl. No. 12/520,483 inventors Andersch, W., et al., filed Jun. 19, 2009 (Not Yet Published).

Co-pending U.S. Appl. No. 12/521,874, inventors Suty-Heinze, A., et al., filed Jul. 1, 2009 (Not Yet Published).

Office Action mailed Jan. 29, 2007, in U.S. Appl. No. 11/482,087 to Rosinger, C., et al.

Amendment and Reply dated May 29, 2007, in U.S. Appl. No. 11/482,087 to Rosinger, C., et al.

Office Action mailed Mar. 5, 2008, in U.S. Appl. No. 11/482,087 to Rosinger, C., et al.

Amendment and Reply dated Sep. 5, 2008, in U.S. Appl. No. 11/482,087 to Rosinger, C., et al.

Office Action mailed Dec. 22, 2008, in U.S. Appl. No. 11/482,087 to Rosinger, C., et al.

Amendment and Reply Jan. 22, 2010, in U.S. Appl. No. 11/482,087 to Rosinger, C., et al.

Office Action mailed Feb. 19, 2010, in U.S. Appl. No. 11/482,087 to Rosinger, C., et al.

Office Action mailed Jan. 27, 2010, in U.S. Appl. No. 11/793,763 to Krohn, P.-W., et al.

Office Action mailed Feb. 22, 2007, in U.S. Appl. No. 11/284,246 to Dutzmann, S., et al.

Amendment and Reply dated Aug. 17, 2007, in U.S. Appl. No. 11/284,246 to Dutzmann, S., et al.

Office Action mailed Nov. 15, 2007, in U.S. Appl. No. 11/284,246 to Dutzmann, S., et al.

Amendment and Reply dated May 13, 2008, in U.S. Appl. No. 11/284,246 to Dutzmann, S., et al.

Office Action mailed Aug. 15, 2008, in U.S. Appl. No. 11/284,246 to Dutzmann, S., et al.

Amendment and Reply Feb. 13, 2009, in U.S. Appl. No. 11/284,246 to Dutzmann, S., et al.

Office Action mailed May 29, 2009, in U.S. Appl. No. 11/284,246 to Dutzmann, S., et al.

Amendment and Reply dated Oct. 27, 2009, in U.S. Appl. No. 11/284,246 to Dutzmann, S., et al.

Office Action mailed Jan. 6, 2010, in U.S. Appl. No. 11/284,246 to Dutzmann, S., et al.

Notice of Opposition submitted to the European Patent Office in co-pending European Application No. 95926913.5, dated Sep. 24, 2006.

Reply to the Notice of Opposition submitted to the European Patent Office in co-pending European Application No. 95926913.5, dated May 14, 2007.

Unverified English language translation of Reply to the Notice of Opposition submitted to the European Patent Office in co-pending European Application No. 95926913.5, dated May 14, 2007.

Grounds of the Decision (Annex)—Opposition issued by the European Patent Office in co-pending European Application No. 95926913.5, dated May 11, 2008.

Unverified English language translation of the Grounds of the Decision (Annex)—Opposition issued by the European Patent Office in co-pending European Application No. 95926913.5, dated May 11, 2008.

Statement of Grounds of Appeal submitted to the European Patent Office in co-pending European Application No. 95926913.5, dated Mar. 16, 2009.

Unverified English language translation of the Statement of Grounds of Appeal submitted to the European Patent Office in co-pending European Application No. 95926913.5, dated Mar. 16, 2009.

Rummens, F.H.A., "An Improved Definition of Synergistic and Antagonistic Effects," *Weed Science* 23:4-6, Weed Science Society of America, United States (1975).

Co-pending Application, U.S. Appl. No. 12/822,256, inventors Davies, P.H., et al., filed on Jun. 24, 2010 (Not Yet Published).

Co-pending Application, U.S. Appl. No. 12/822,261, inventors Davies, P.H., et al., filed on Jun. 24, 2010 (Not Yet Published).

Co-pending Application, U.S. Appl. No. 12/831,990, inventors Suty-Heinze, A., et al., filed on Jul. 7, 2010 (Not Yet Published).

Co-pending Application, U.S. Appl. No. 12/881,281, inventors Seitz, T., et al., filed on Sep. 14, 2010 (Not Yet Published).

Co-pending Application, U.S. Appl. No. 12/879,758, inventors Stork, A., et al., filed on Sep. 10, 2010 (Not Yet Published).

* cited by examiner

COMPOSITIONS FOR THE CONTROL OF PLANT PESTS

BACKGROUND OF THE INVENTION

1. Field of the Invention

The present invention relates to pest control compositions which contain an active compound combination of certain agonists or antagonists of the nicotinic acetylcholine receptors of insects together with fungicides, their preparation and their use for the control of plant pests.

2. Description of the Related Art

Agonists or antagonists of the nicotinic acetylcholine receptors of insects are known, for example from the following publications:

European Published Specifications No. 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 455 000, 135 956, 471 372, 302 389; German Published Specifications No. 3 639 877, 3 712 307; Japanese Published Specifications No. 03 220 176, 02 207 083, 63 307 857, 63 287 764, 03 246 283, 04 9371, 03 279 359, 03 255 072; U.S. Pat. Nos. 5,034,524, 4,948,798, 4,918,798, 4,918,086, 5,039,686, 5,034,404; PCT Applications No. WO 91/17 659, 91/4965; French Application No. 2 611 114; Brazilian Application No. 88 03 621.

The methods, processes, formulae and definitions described in these publications, and also the specific preparations and compounds described therein, are expressly incorporated herein.

Fungicidal active compounds, such as azole derivatives, aryl benzyl ethers, benzamides, morpholine compounds and other heterocycles are known (cf. K. H. Büchel "Pflanzenschutz and Schädlingsbekämpfung [Crop protection and pest control]", pages 140 to 153, Georg Thieme-Verlag, Stuttgart 1977, EP-OS (European Published Specification) 0 040 345, DE-OS (German Published Specification) 3 324 010, DE-OS (German Published Specification) 2 201 063, EP-OS (European Published Specification) 0 112 284, EP-OS (European Published Specification) 0 304 758, and DD-PS (German Democratic Republic Patent Specification) 140 412).

Mixtures of certain nitromethylene derivatives with fungicidal active compounds and their use as compositions for the control of pests in crop protection are already known (U.S. Pat. No. 4,731,385; JP-OS (Japanese Published Specifications) 63-68507, 63/68505, 63/72 608, 63/72 609, 63/72 610). Mixtures of certain open-chain nitromethylenes and nitroguanidines with fungicides are already known (JP-OS (Japanese Published Specification) 30 47 106; U.S. Pat. No. 5,181,587).

Mixtures of cyclopropylcarboxamides with certain nitromethylenene or nitroguanidine derivatives are already known (JP-OS (Japanese Published Specification) 3 271 207;

Mixtures of inter alia imidacloprid and fungicidal active compounds for use in material protection and against termites, but not for use against plant-damaging pests, are already known (EP-OS (European Published Specification) (Nit 259)). Mixtures of imidacloprid and azolylmethylcycloalkanes, in particular triticonazole, are known from EP-OS (European Published Specification) 545 834.

However, nothing is yet known about nitroguanidine derivatives and fungicides other than cyclopropylcarboxamides and triticonazole influencing each other so favourably in over action that, while being well tolerated by plants, they can be used with outstanding effect as compositions for the control of plant pests.

DETAILED DESCRIPTION OF THE INVENTION

The present invention relates to plant pest control compositions which contain compounds of the the general formula (I)

in which
X represents —CH= or =N—,
E represents an electron-withdrawing radical, in particular nitro or cyano,
R represents optionally substituted hetarylalkyl,
A represents hydrogen, alkyl, or a bifunctional group which is linked to the radical Z,
Z represents alkyl, —NH, alkyl, —N(alkyl)$_2$ or a bifunctional group which is linked to the radical A, in mixtures with fungicidal active compounds, excluding cyclopropylcarboxamide derivatives and azolylmethylcloalkanes.

Preferably, the invention relates to plant pest control compositions which contain compounds of the formula (I) in which the radicals have the following meaning:
X represents =CH— or =N—,
E represents NO$_2$ or CN,
R represents hetarylmethyl, hetarylethyl having up to 6 ring atoms and N, O, S, in particular N, as heteroatoms.

In particular there may be mentioned thienyl, furyl, thiazolyl, imidazolyl, pyridyl, which are optionally substituted.

Preferred examples of substituents are:
alkyl having preferably 1 to 4, in particular 1 or 2 carbon atoms, such as methyl, ethyl, n- and i-propyl and n-, i- and t-butyl; alkoxy having preferably 1 to 4, in particular 1 or 2 carbon atoms, such as methoxy, ethoxy, n- and i-propyloxy and n-, i- and t-butyloxy; alkylthio having preferably 1 to 4, in particular 1 or 2 carbon atoms, such as methylthio, ethylthio, n- and i-propylthio and n-, i- and t-butylthio; haloalkyl having preferably 1 to 4, in particular 1 or 2 carbon atoms and preferably 1 to 5, in particular 1 to 3 halogen atoms, wherein the halogen atoms are identical or different and wherein the halogen atoms are preferably fluorine, chlorine or bromine, in particular fluorine, such as trifluoromethyl; hydroxyl; halogen, preferably fluorine, chlorine, bromine and iodine, in particular fluorine, chlorine and bromine; cyano; nitro; amino; monoalkyl- and dialkylamino having preferably 1 to 4, in particular 1 or 2 carbon atoms per alkyl group, such as methylamino, methylethylamino, n- and i-propylamino and methyl-n-butylamino;
A represents hydrogen, C$_{1-4}$alkyl, in particular methyl or ethyl,
Z represents C$_{1-4}$alkyl, in particular ethyl or methyl, —NH (C$_{1-4}$alkyl), —N(C$_{1-4}$ alkyl) or
A and Z, form together with the atoms to which they are bonded, form a saturated or unsaturated heterocyclic ring. The heterocyclic ring may contain a further 1 or 2 identical or different heteroatoms and/or heterogroups. Preferably, heteroatoms are oxygen or nitrogen and heterogroups are N-alkyl, the alkyl of the N-alkyl group containing preferably 1 to 4, in particular 1 or 2 carbon atoms. Examples of alkyl include methyl, ethyl, n- and i-propyl and n-, i- and t-butyl. The heterocyclic ring contains 5 to 7, preferably 5 or 6 ring members.

Examples of the heterocyclic ring include pyrrolidine, piperidine, thiazolidine, piperazine, imidazolidine, hexamethyleneimine, hexahydro-1,3,5-triazine, morpholine, which may optionally be substituted, preferably by methyl.

Most preferred are compounds of the general formulae (I) and (Ib)

(Ia)

(Ib)

in which n represents 1 or 2,

Subst. represents one of the abovementioned substituents, in particular halogen, especially chlorine, A and Z have the abovementioned preferred meanings, Specifically, the following compounds may be mentioned:

-continued

Fungicides in the novel compositions for the control of plant pests are for example:

(1) Azole derivatives of the formula (II)

(II-1)

$R^1 =$ Cl—⟨phenyl⟩—$(CH_2)_2$—, $R^2 =$ —$C(CH_3)_3$, (TEBUCONAZOLE)

$R^3 =$ OH, n = 1, (II-2)

$R^1 =$ Cl—⟨phenyl⟩(Cl)—, (PROPICONAZOLE)

$R^2, R^3 =$ —$OCH_2CH(n\text{-}C_3H_7)O$—, n = 1, (II-3)

$R^1 =$ Cl—⟨phenyl⟩—O—⟨phenyl⟩(Cl)—, n = 1, $R^2, R^3 =$ —$OCH_2CH(CH_3)O$—, (DIFENCONAZOLE)

(II-4)

$R^1 =$ Cl—⟨phenyl⟩—, $R^2 =$ —CH—$CH_3$, ⟨cyclopropyl⟩

(CYPROCONAZOLE)

$R^3 =$ —OH, n = 1, (II-5)

$R^1 =$ F—⟨phenyl⟩—, $R^2 =$ ⟨fluorophenyl⟩—, (FLUTRIAFOL)

$R^3 =$ OH, n = 1,

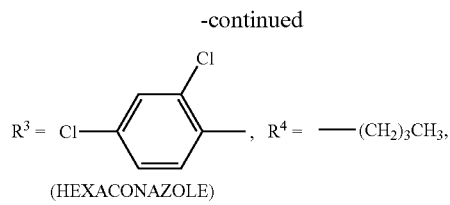
(HEXACONAZOLE)
$R^5$ = OH, n = 1,
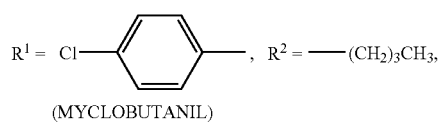
(MYCLOBUTANIL)
$R^3$ = CN, n = 1,
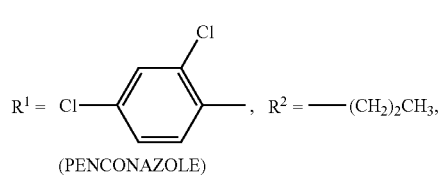
(PENCONAZOLE)
$R^3$ = H, n = 1,
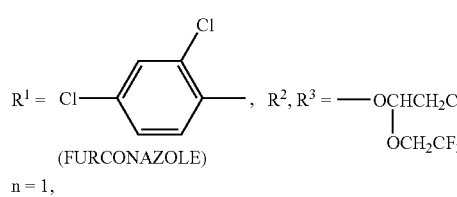
(FURCONAZOLE)
n = 1,
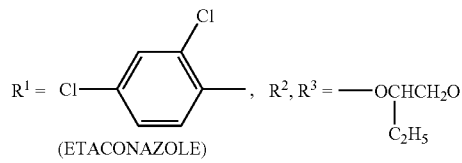
(ETACONAZOLE)
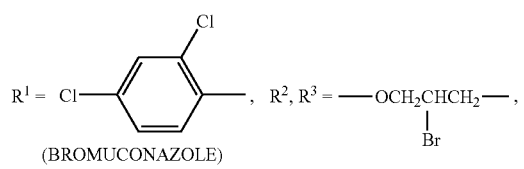
(BROMUCONAZOLE)
n = 1,
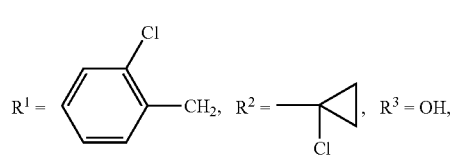
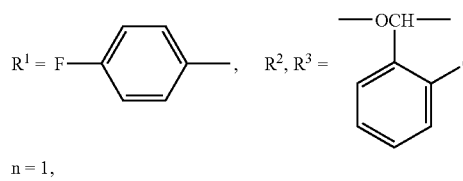
n = 1,
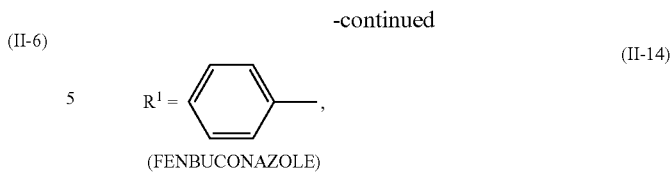
(FENBUCONAZOLE)
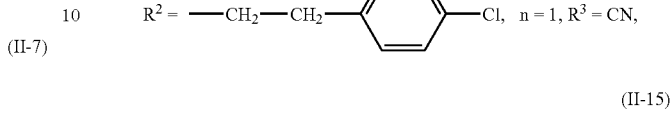
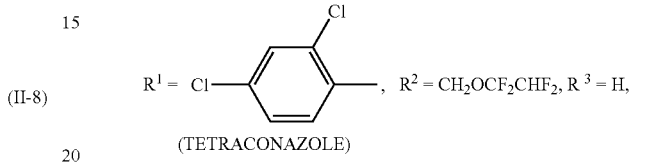
(TETRACONAZOLE)
n = 1,
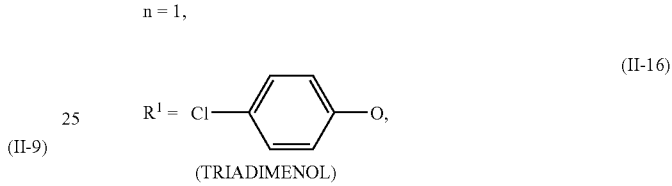
(TRIADIMENOL)
$R^2$ = —CH(OH)—C(CH$_3$)$_3$, n = 0, $R^3$ = H,
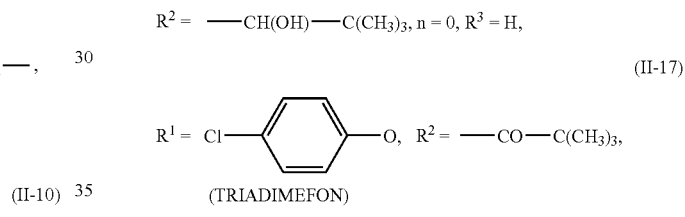
(TRIADIMEFON)
n = 0, $R^3$ = H,
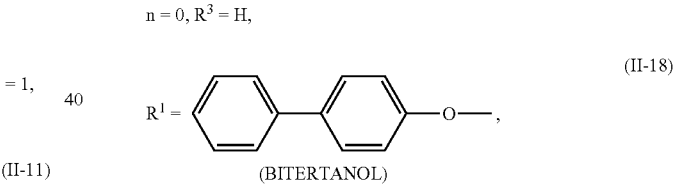
(BITERTANOL)
$R^2$ = —CH(OH)—C(CH$_3$)$_3$, n = O, $R^3$ = H,
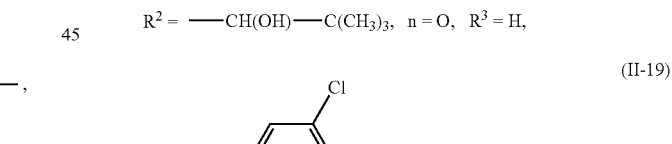
(DICLOBUTRAZOL)
$R^2$ = —CH(OH)—C(CH$_3$)$_3$, n = O, $R^3$ = H
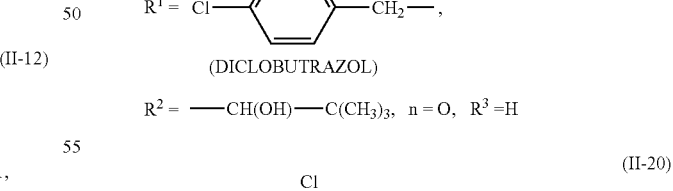
(DINICONAZOLE)
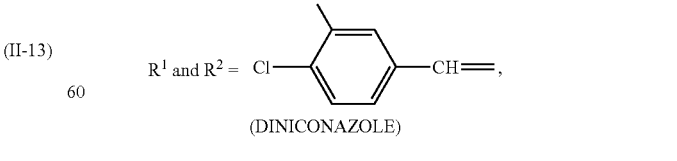
n = 0,
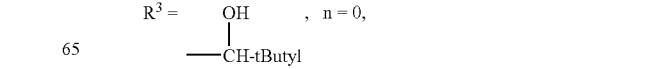

(2) Azole derivatives of the formula

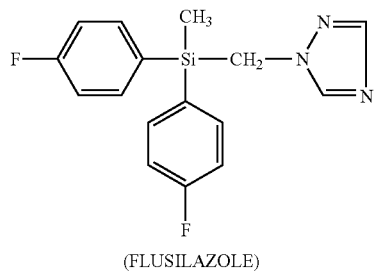

(FLUSILAZOLE)

(III)

(3) The azole derivative of the formula

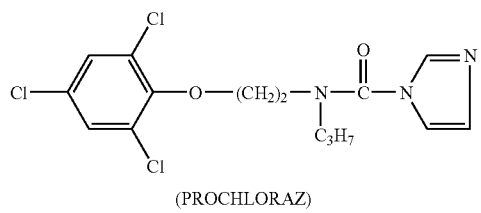

(PROCHLORAZ)

(IV)

(4) The compound $S_x$ (V)

(5) Azole derivative of the formula

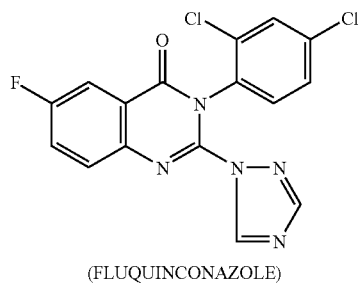

(FLUQUINCONAZOLE)

(VI)

(6) Heterocycles of the formula

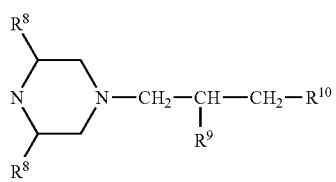

(VII)

X = O, $R^8$ = $CH_3$, $R^9$ = H, $R^{10}$ = $C_{10}H_{21}$
(TRIDEMORPH) (VII-1)

X = O, $R^8$ = $CH_3$, $R^9$ = H, $R^{10}$ = $C_9H_{19}$
(ALDIMORPH) (VII-2)

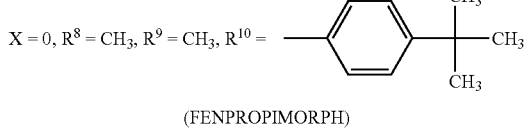

(FENPROPIMORPH) (VII-3)

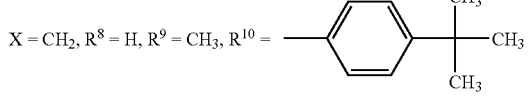

(FENPROPIDIN) (VII-4)

(7) Compound of the formula

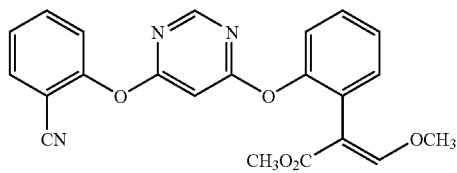

(VIII)

(8) Compound of the formula

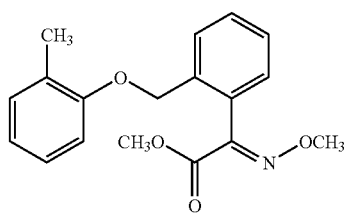

(IX)

(9) Compound of the formula

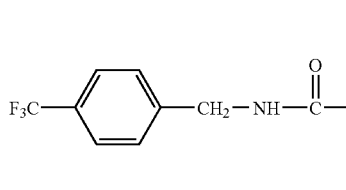

(X)

(10) Compound of the formula

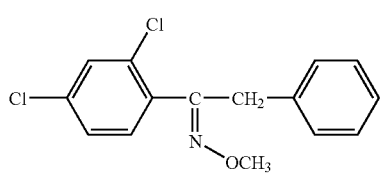

(PYRIFENOX)

(XI)

(11) Compound of the formula

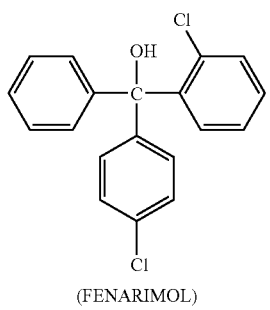

(FENARIMOL)

(12) Compound of the formula

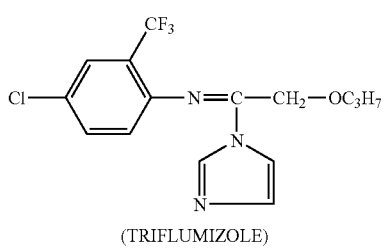

(TRIFLUMIZOLE)

(13) Compounds of the formula

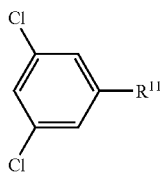

(XIII)

$R^{11} =$ 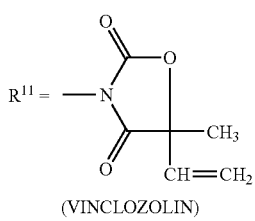

(VINCLOZOLIN)   (XIV-1)

$R^{11} =$ 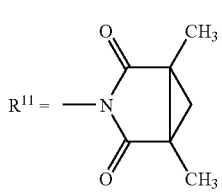

(PROCYMIDONE)   (XIV-2)

$R^{11} =$ 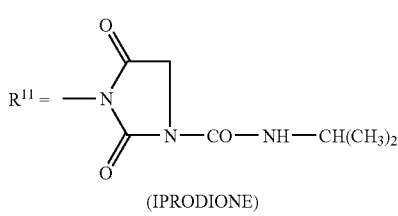

(IPRODIONE)   (XIV-3)

(14) Compounds of the formula

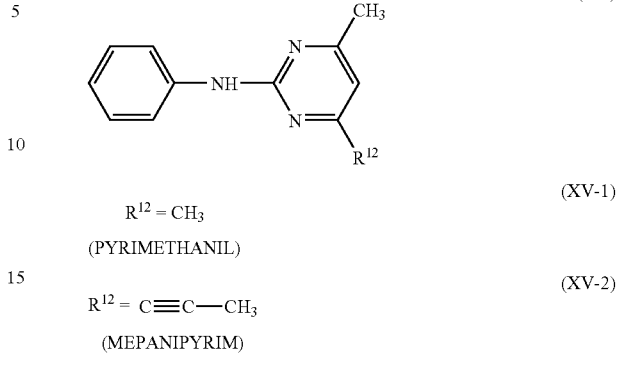

(XIV)

$R^{12} = CH_3$   (XV-1)

(PYRIMETHANIL)

$R^{12} = C \equiv C — CH_3$   (XV-2)

(MEPANIPYRIM)

(15) Compounds of the formula

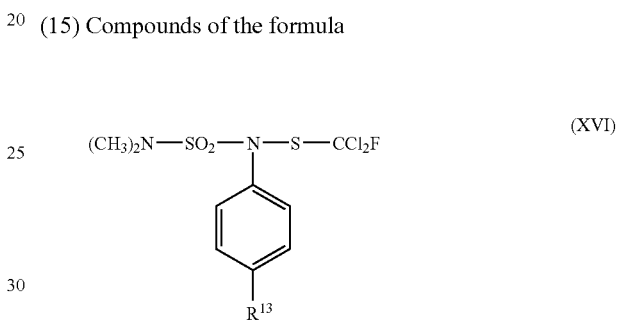

(XVI)

$R^{13} = H$   (XVI-1)

(DICHLORFLUANID)

$R^{13} = CH_3$   (XVI-2)

(TOLYLFLUANID)

(16) Compound of the formula

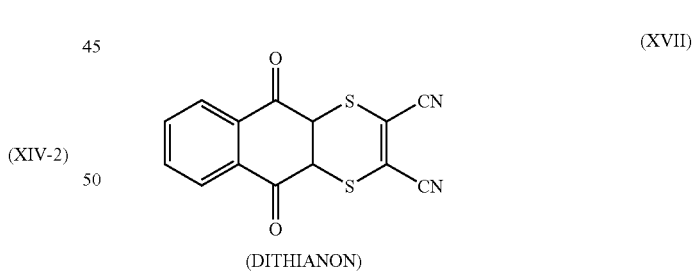

(XVII)

(DITHIANON)

(17) Compound of the formula

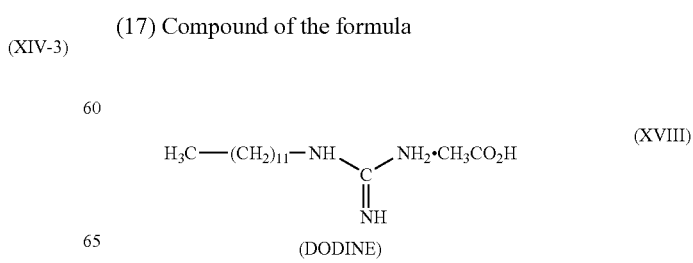

(XVIII)

(DODINE)

(18) Compound of the formula
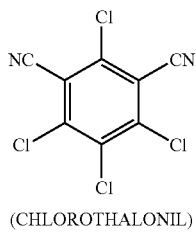
(CHLOROTHALONIL)
(19) Compound of the formula
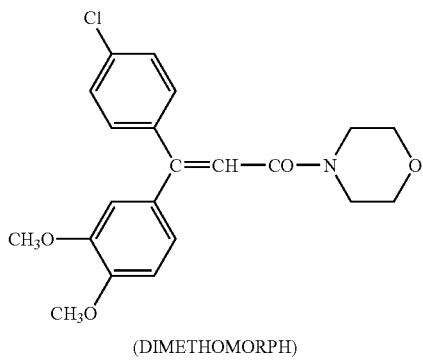
(DIMETHOMORPH)
(20) Compound of the formula
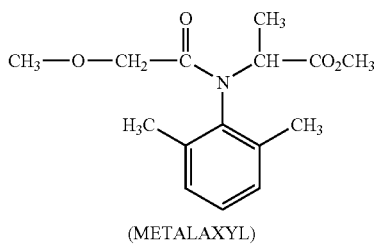
(METALAXYL)
(21) Compound of the formula
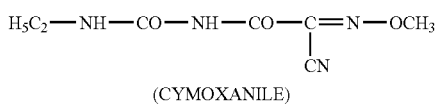
(CYMOXANILE)
(22) Compound of the formula
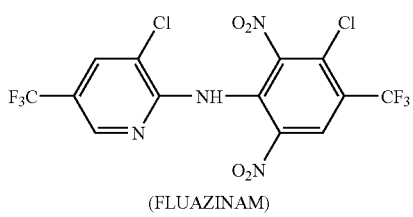
(FLUAZINAM)
(23) Compound of the formula
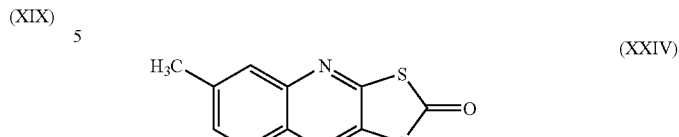
(24) Compounds of the formula
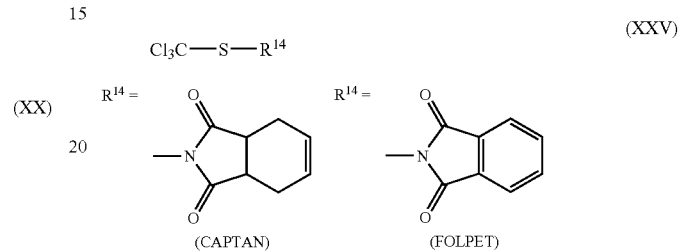
(25) Compound of the formula
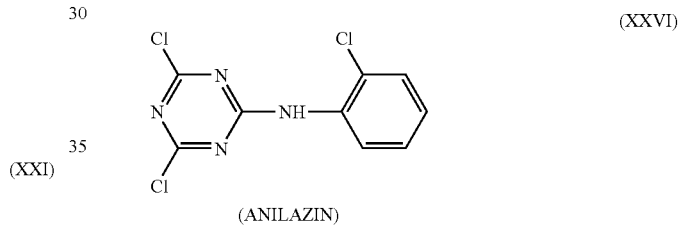
(ANILAZIN)
(26) Compound of the formula
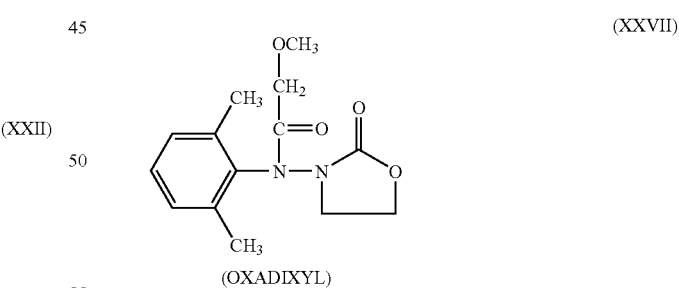
(OXADIXYL)
(27) Compound of the formula
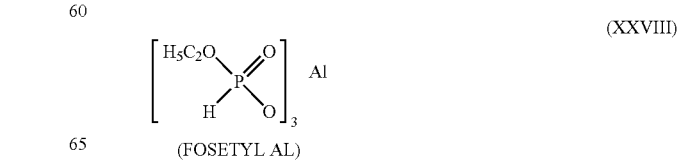
(FOSETYL AL)

(28) Compound of the formula (DINOCAP) (XXIX)

(29) Compound of the formula (XXX)

(30) Compound of the formula (XXXI)

(31) Compound of the formula (ANTRACOL) (XXXII)

(32) Compounds of the formula (XXXIII)

M = Zn (ZINEB) (XXXIII-1)
M = Mn (MANEB) (XXXIII-2)
M = Mn/Zn (Mancozeb) (XXXIII-3)

(33) Compound of the formula (THIRAM) (XXXIV)

(34) Compound of the formula (TYMIBENCONAZOLE) (XXXV)

(35) Compound of the formula $$[[(S-CS-NH-CH_2-CH_2-NH-CS-S-)\cdot Zn(NH_3)_3)] \atop (-S-CS-NH-CH_2-CH_2-NH-CS-S-)]_y$$

(METIRAM) (XXXVI)

(36) Compound of the formula (XXXVII)

(37) Compound of the formula (XXXVIII)

(38) Compounds of the formula (XXXIX)

in which

R$^{15}$ and R$^{16}$, independently of each other, represent hydrogen, halogen, methyl or phenyl, and R$^{17}$ represents hydrogen or methyl,

(39) 8-'Butyl-2-(N-ethyl-N-n-propylamino)-methyl-1,4-dioxaspiro[4.5]decane of the formula (XL)

[Structure: spiro compound with C(CH$_3$)$_3$ on cyclohexane, dioxolane ring, CH$_2$-N(C$_2$H$_5$)(CH$_2$CH$_2$CH$_3$)]

(40) Compound of the formula

[Structure: F-C$_6$H$_4$-CH$_2$-C(CH$_3$)-(CH$_2$OSO$_2$CH$_3$)$_2$]

(41) Compound of the formula.

[Structure: 7-chloro-benzotriazine N-oxide with imidazole substituent]

(42) Compound of the formula

[Structures labeled with A=]

A= [methylbenzodioxole-CF$_2$] — Fludioxonil

A= [methyl-dichlorophenyl] — Fenpiclonil

A= [methyl-fluoro-trifluoromethyl phenyl]

(43) Compound of the formula

[Structure: tBu-C$_6$H$_4$-CH$_2$-CH(CH$_3$)-CH$_2$-N(piperidine)]

(44) Benzimidazole of the formula

[Benzimidazole structure with R$^9$ and R$^6$]

R$^9$ = CONHtBu; R$^6$ = —NHCOOMe
Benomyl

R$^9$ = H; R$^6$ = [thiazoline ring]
Thiabendazole

R$^9$ = H; R$^6$ = —NHCOOMe
Carbendazin

(45) Compound of the formula

[Structure: benzene-1,2-di(NH—CS—NHCOOMe)]

(46) Compound of the formula $$HN-[(CH_2)_8NH-\overset{NH}{\underset{}{C}}-NH_2]_2$$

(47) Compound of the formula

[Structure: pentachloronitrobenzene]

The active compounds of the formula (I) are known for example from EP-OS (European Published Specification) 192 060.

The fungicidal active compounds are also known.

In the following publications, for example, there are described:

(1) Compounds of the formula (II)

DE-OS (German Published Specification) 2 201 063

DE-OS (German Published Specification) 2 324 010

DE-OS (German Published Specification) 2 737 489

DE-OS (German Published Specification) 3 018 866

DE-OS (German Published Specification) 2 551 560
EP 47 594
DE 2 735 872
(2) Compound of the formula (III)
EP 68 813
U.S. Pat. No. 4,496,551
(3) Compound of the formula (IV)
DE-OS (German Published Specification) 2 429 523
DE-OS (German Published Specification) 2 856 974
U.S. Pat. No. 4,108,411
(6) Compounds of the formula (VII)
DL 140 041
(7) Compound of the formula (VIII)
EP 382 375
(8) Compound of the formula (IX)
EP 515 901
(9) Compound of the formula (X)
EP 314 422
(10) Compound of the formula (XI)
EP 49 854
(11) Compound of the formula (XII)
DE-OS (German Published Specification) 1 770 288
U.S. Pat. No. 3,869,456
(13) Compounds of the formula (XIV)
DE 2 207 576
U.S. Pat. No. 3,903,090
U.S. Pat. No. 3,755,350
U.S. Pat. No. 3,823,240
(14) Compounds of the formula (XV)
EP 270 111
(19) Compound of the formula (XX)
EP 219 756
(34) Compound of the formula (XXXV)
U.S. Pat. No. 4,512,989
(38) Compounds of the formula (XXXIX)
EP 398 692

Compounds of groups (15), (16), (17), (18), (23), (34), (25), (28), (31), (32), (33) and (38) to (47) are described for example in K. H. Büchel, "Pflanzenschutz and Schädlingsbekämpfung [Crop protection and pest control]", pages 121-153, Georg Thieme-Verlag, Stuttgart, 1977. The compound of group (39) is known from EP-OS (European Published Specification) 281 842.

Besides the active compound of the formula (I), the active compound combinations according to the invention contain at least one fungicidal active compound, selected for example from the compounds of groups (1) to (47). Additionally, they may also contain other active compounds and also customary auxiliaries and additives and diluents.

A synergistic effect is particularly apparent when the active compounds in the active compound combinations according to the invention are present in particular weight ratios. However, the weight ratios of the active compounds in the active compound combinations can be varied within a relatively wide range. In general
0.1 to 10 parts by weight, preferably
0.3 to 3 parts by weight, of at least one fungicidal active compound from the groups (1) to (48) is/are allocated to one part by weight of active compound of the formula (I).

The combinations of active compounds according to the invention possess very good fungicidal properties. They can be employed, in particular, for controlling phytopathogenic fungi, such as Plasmodiophoromycetes, Oomycetes, Chytridiomycetes, Zygomycetes, Ascomycetes, Basidiomycetes, Deuteromycetes etc.

The active compound combinations according to the invention are particularly suitable for controlling cereal diseases, such as Erysiphe, Cochliobolus, Septoria, Pyrenophora and Leptosphaeria, and for use against fungal infestations of vegetables, grapes and fruit, for example against Venturia or Podosphaera on apples, Uncinula on vine plants or Sphaeroteca on cucumbers.

The active compound combinations are also suitable for controlling animal pests, preferably anthropods, in particular insects encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germancia, Acheta domesticus, Gryllotalpa* spp., *Locusta migratoria migratorioides, Melanoplus differentialis* and *Schistocerca gregaria.* From the order of the *Dermaptera,* for example, *Forficula auricularia.*

From the order of the *Isoptera,* for example, *Reticulitermes* spp.

From the order of the Anoplura, for example, *Pediculus humanus corporis, Haematopinus* spp. and *Linognathus* spp.

From the order of the Mallophaga, for example, *Trichodectes* spp. and *Damalinea* spp. From the order of the Thysanoptera, for example, *Hercinothrips femoralis* and *Thrips tabaci.*

From the order of the Heteroptera, for example, *Eurygaster* spp., *Dysdercus intermedius, Piesma quadrata, Cimex lectularius, Rhodnius prolixus* and *Triatoma* spp.

From the order of the *Homoptera,* for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Phylloxera vastrix, Pemphigus* spp., *Empoasca* spp., *Euscelis bilobatus, Nephotettix cincticeps, Lecanium corn, Saissetia oleae, Laodelphax striatellus, Nilaparvata lugens, Aonidiella aurantii, Aspidiotus hederae, Pseudococcus* spp. and *Psylla* spp.

From the order of the *Lepidoptera,* for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp. *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fiuniferana, Clysia ambiguella, Homona magnanima* and *Tortrix viridana.*

From the order of the Coleoptera, for example, *Anobium punctatum, Rhizopertha dominica, Bruchidius obtectus,*

*Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, C euthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica.*

From the order of the *Hymenoptera*, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa.*

The fact that the active compound combinations are well tolerated by plants at the concentrations required for controlling plant diseases permits a treatment of aerial parts of plants, of propagation stock and seeds, and of the soil.

The active compounds of the invention can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite; as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound combinations according to the invention can be present in the formulations as mixtures with other known active compounds, such as fungicides, insecticides, acaricides and herbicides, and also as mixtures with fertilizers or plant growth regulators.

The active compound combinations can be used as such, in the form of their formulations or as the use forms prepared therefrom, such as ready-to-use solutions, emulsifiable concentrates, emulsions, suspensions, wettable powders, soluble powders and granules.

They are used in the customary manner, for example by watering, spraying, atomizing, scattering, brushing on and as a powder for dry seed treatment, a solution for seed treatment, a water-soluble powder for seed treatment, a water-soluble powder for slurry treatment, or by encrusting.

In the treatment of parts of plants, the concentrations of active compound in the use forms can be varied within a substantial range. In general, they are between 1 and 0.0001% by weight, preferably between 0.5 and 0.001%.

In the treatment of seed, amounts of 0.001 to 50 g of active compound per kilogram of seed are generally required, preferably 0.01 to 10 g.

In the treatment of the soil, active compound concentrations from 0.00001 to 0.1% by weight, preferably 0.0001 to 0.02% by weight, are required at the site of action.

The good fungicidal activity of the active compound combinations according to the invention can be seen from the examples which follow. While the individual active compounds or the known active compound combinations show weaknesses with regard to the fungicidal activity, the tables of the examples which follow show clearly that the activity found in the case of the active compound combinations according to the invention exceeds the total of the activities of individual active compounds and also exceeds the activities of the known active compound combinations.

In the examples that follow, imidacloprid is employed as active compound of the formula (I). The fungicidal active compounds also used are stated in the examples.

Example A

Drechslera Graminea Test (Barley)/Seed Treatment (syn. Helminthosporium Gramineum)

The active compounds are used as a powder for dry seed treatment. They are prepared by extending the active compound in question with rock meal to give a finely pulverulent mixture which ensures uniform distribution on the seed surface.

To carry out the seed treatment, the infected seed and the seed-dressing product are shaken for 3 minutes in a sealed glass flask.

The seed, embedded in screened, moist standard soil in sealed Petri dishes, is exposed to a temperature of 4° C. for 10 days in a refrigerator. This triggers germination of the barley and, if appropriate, of the fungal spores. 2×50 pregerminated barley kernels are subsequently sown in standard soil at a depth of 3 cm and grown in a greenhouse at a temperature of approximately 18° C. in seed boxes which are exposed to the light for 15 hours per day.

Approximately 3 weeks after sowing, the plants are evaluated for symptoms of barley leaf stripe.

Mixtures of imidacloprid with tebuconazole, captan, euparen M, bitertanol, triazoxide, thiram, fludioxonil exhibit a pronounced increase in activity as compared with treatment using the individual compounds.

Example B

Fusarium Nivale Test (Wheat)/Seed Treatment

The active compounds are used as a powder for dry seed treatment. They are prepared by extending the active compound in question with rock meal to give a finely pulverulent mixture which ensures uniform distribution on the seed surface.

To carry out the seed treatment, the infected seed and the seed-dressing product are shaken for 3 minutes in a sealed glass flask.

2×100 wheat kernels are subsequently sown in standard soil at a depth of 1 cm and grown in the greenhouse at a temperature of approximately 10° and a relative atmospheric humidity of approximately 95% in seed boxes which are exposed to the light for 15 hours per day.

Approximately 3 weeks after sowing, the plants are evaluated for snow blight symptoms.

Mixtures of imidacloprid with euparen, guazatine, triadimenol, difenconazole, fenpiclonil exhibit a pronounced increase in activity as compared with treatment using the individual compounds.

Example C

Phaedon Larvae Test

Solvent: 7 parts by weight of dimethylformamide
Emulsifier: 1 part by weight of alkylaryl polyglycol ether
To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After 7 days the destruction in % is determined.

Mixtures of imidacloprid with anilazine, benomyl, bitertanol, captan, diclofluanid, mancozeb, maneb, metalaxyl, prochloraz, procymidone, sulphate, tolylfluanid, triadimefon, triadimenol exhibit a pronounced increase in activity as compared with treatment using the individual compounds.

Example D

Myzus Test

Solvent: 7 parts by weight of dimethylformamide
Emulsifier: 1 part by weight of alkylaryl polyglycol ether
To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) heavily infested with aphids (*Myzus persicae*) are treated by dipping in the preparation of active compound of the desired concentration.

After 6 days, the destruction in % is determined.

Mixtures of imidacloprid with bitertanol, fenpropimorph, prochloraz, tebuconazole exhibit a pronounced increase in activity as compared with treatment using the individual compounds.

Example E

Botrytis Test (Beans)/Protective

Solvent: 4.7 parts by weight of acetone
Emulsifier: 0.3 parts by weight of alkylaryl polyglycol ether
To produce a suitable preparation of active compound, 1 part by weight of active compound is mixed with the stated amount of solvent and the stated amount of emulsifier, and the concentrate is diluted with water to the desired concentration.

To test for protective activity, young plants are sprayed with the preparation of active compound until dripping wet. After the spray coating has dried on, two small pieces of agar covered with Botrytis cinerea are placed on each leaf. The inoculated plants are placed in a darkened humid chamber at 20° C. 3 days after the inoculation, the size of the infected spots on the leaves is evaluated.

Mixtures of imidacloprid with procymidone, tolyfluanid, tebuconazole exhibit a pronounced increase in activity as compared with treatment using the individual compounds.

Example F

Podosphaera Test (Apple)/Protective

Solvent: 4.7 parts by weight of acetone
Emulsifier: 0.3 parts by weight of alkylaryl polyglycol ether
To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated by dusting with conidia of the causative organism of apple mildew (*Podosphaera leucotricha*).

The plants are then placed in a greenhouse at 23° C. and a relative atmospheric humidity of about 70%.

Evaluation is carried out 10 days after the inoculation.

Mixtures of imidacloprid with fenpropidin, triadimenol exhibit a prounced increase in activity as compared with treatment using the individual compounds.

What is claimed is:

1. A composition comprising

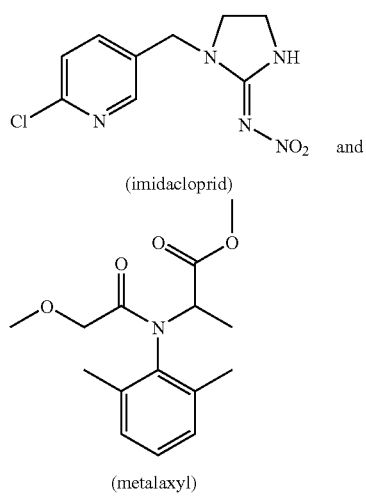

(imidacloprid)

and (metalaxyl)

with the proviso that the composition does not contain thiram or fludioxonil.

2. The composition of claim 1, comprising 0.1 to 10 parts by weight of metalaxyl per part by weight of imidacloprid.

3. The composition of claim 1, comprising 0.3 to 3 parts by weight of metalaxyl per part by weight of imidacloprid.

4. The composition of claim 1, further comprising at least one solid carrier.

5. The composition of claim 4, wherein the solid carrier is selected from the group consisting of kaolin, clay, talc, chalk, quartz, attapulgite, montmorillonite earth, diatomaceous earth, silica, alumina, and silicate.

6. The composition of claim 1, further comprising at least one extender or surface-active agent.

7. A method of controlling phytopathogenic fungi, comprising contacting said fungi with an effective amount of the composition of claim 1.

8. A method of controlling plant disease, comprising contacting aerial parts of a plant, propagation stock, seed, or soil with an effective amount of the composition of claim 1.

9. The method of claim 8, wherein imidacloprid or metalaxyl is applied to said parts of a plant at a concentration of 1 to 0.0001% by weight.

10. The method of claim 8, wherein from 0.001 to 50 g of imidacloprid or metalaxyl is applied per kilogram of said seed.

11. The method of claim 8, wherein imidacloprid or metalaxyl is applied to the soil at a concentration of 0.00001 to 0.1% by weight.

12. A method of controlling plant insects, comprising contacting said insects with an effective amount of the composition of claim 1.

* * * * *